United States Patent [19]

Salmon et al.

[11] Patent Number: 4,988,733

[45] Date of Patent: Jan. 29, 1991

[54] N-[1-(3-PHENOXYPHENYL)ETHYL-]ACETOHYDROXAMIC ACID COMPOUNDS WHICH ARE USEFUL ANTI-INFLAMMATORY AGENTS

[75] Inventors: John A. Salmon; William P. Jackson, both of Beckenham, England

[73] Assignee: Burroughs Wellcome Co., Research Triangle Park, N.C.

[21] Appl. No.: 219,096

[22] Filed: Jul. 14, 1988

[30] Foreign Application Priority Data

Jul. 15, 1987 [GB] United Kingdom ................. 8716640
Feb. 3, 1988 [GB] United Kingdom ................. 8802378
Mar. 16, 1988 [GB] United Kingdom ................. 8806278

[51] Int. Cl.$^5$ .................... C07C 83/10; A61K 31/185
[52] U.S. Cl. ..................................... 514/575; 562/621
[58] Field of Search ................ 514/575; 260/500.5 H; 562/623, 621

[56] References Cited

U.S. PATENT DOCUMENTS 4,738,986 4/1988 Kneen et al. ..................... 514/575

OTHER PUBLICATIONS

J. Med. Chem. 1988, p. 3–5, Orally Active Hydroxamic Acid Inhibitors of Leukotriene Biosynthesis, Summers et al.

*Primary Examiner*—Mary C. Lee
*Assistant Examiner*—Zinna Northington-Davis
*Attorney, Agent, or Firm*—Donald Brown

[57] ABSTRACT

The present invention provides compounds of formula (II)

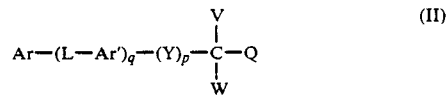

wherein
q is 1, and p is 1;
Ar is phenyl optionally substituted by one or more substitutents independently selected from $C_{1-4}$alkyl (which may be substituted by one or more halogen atoms) and halogen;
L is —O—;
Ar' is 1,3- or 1,4-phenylene;
Y is (E)—CH=CH—;
V is hydrogen or $C_{1-4}$alkyl;
W is $C_{1-4}$alkyl; and
Q is a moiety of formula

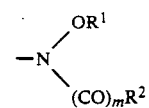

wherein m is 1, $R^1$ is hydrogen, and $R^2$ is hydrogen or $C_{1-4}$alkyl;
and salts thereof, processes for the preparation of these compounds, pharmaceutical formulations containing them, and uses for them in medicine and in other applications.

11 Claims, No Drawings

N-[1-(3-PHENOXYPHENYL)ETHYL]ACETOHYDROXAMIC ACID COMPOUNDS WHICH ARE USEFUL ANTI-INFLAMMATORY AGENTS

The present invention relates to certain compounds which are hydroxamic acid aryl derivatives, to processes for their preparation, to pharmaceutical formulations containing them, and to their use in medicine and in other applications.

A class of agents defined in European Pat. No. 55418 are described therein as dual inhibitors of the lipoxygenase and cyclo-oxygenase enzymes of the mammalian arachidonic acid metabolism and were found to exhibit anti-inflammatory and related activities. Other compounds which have been described as lipoxygenase and/or cyclo-oxygenase inhibitors include certain naphthyloxy derivatives, for example, as described in U.S. Pat. No. 3,740,437 or in Proc. Ann. Symp. Inst. Basic Med. Sci., Royal College of Surgeons of England, October 1982, pp. 263–274. Compounds described in the latter reference include the compound known as nafazatrom.

European patent application No. 86301895 describes a class of compounds which are inhibitors of the lipoxygenase and/or cyclo-oxygenase enzymes. We have now found that within the class of compounds described in the European application, there is a sub-class of compounds whose exceptional activity with regard to the inhibition of lipoxygenase and/or cyclo-oxygenase renders them particularly useful for certain medical and non-medical applications.

According to the European application, there is provided a compound of formula (I)

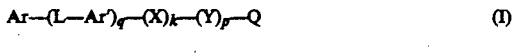

wherein
k, p and q are independently 0 or 1, provided that when k is 1, then p is also 1;
Ar represents either:
(i) naphthyl, tetrahydronaphthyl or pyridyl, any of which is optionally substituted by one or more substituents independently selected from $C_{1-4}$ alkyl (which may be substituted by one or more halogen atoms), $C_{1-4}$ alkoxy, halo, nitro, amino, carboxy, $C_{1-4}$ alkoxycarbonyl and hydroxy, or
(ii) phenyl optionally substituted by one or more substituents independently selected from phenyl (optionally substituted by one or more substituents independently selected from those specified as optional substituents in (i) above) and those optional substituents specified in (i) above;
L is $-(CH_2)_r-$ in which r is 1-4, $-O-$, $-CH_2O-$, $-CH_2S-$, $-OCH_2-$, $-CONH-$, $-NHCO-$, $-CO-$, or $-CH_2NH-$;
Ar' is phenylene, thienylene or pyridylene, any of which is optionally substituted by one or more substituents independently selected from those specified as optional substituents in definition (i) of Ar;
X is oxygen, sulphur or carbonyl, provided that at least one atom separates said carbonyl group from any carbonyl group in Q as defined below;
Y is $C_{1-10}$ alkylene or $C_{2-10}$ alkenylene; and
Q is a moiety selected from groups of formula

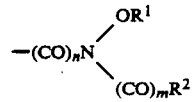

in which one of m and n is 0 and the other is 1,
and when n is 1 and m is 0, $R^1$ and $R^2$ are independently selected from hydrogen and $C_{1-4}$ alkyl, with the possibility that $R^2$ may also be $C_{5-7}$ cycloalkyl,
or when n is 0 and m is 1, $R^1$ is independently selected from hydrogen $C_{1-4}$ alkyl, groups as defined for Ar above and groups of formula $-COR^3$ in which $R^3$ is selected from $C_{1-4}$ alkyl (optionally substituted by a carboxy or $C_{1-4}$ alkoxycarbonyl group) and groups of formula $-N(R^4)R^5$ in which $R^4$ is hydrogen or $C_{1-4}$ alkyl and $R^5$ represents hydrogen, $C_{1-4}$ alkyl, or phenyl optionally substituted by one or more substituents independently selected from those specified as optional substituents in definition (i) of Ar, and $R^2$ is selected from hydrogen, $C_{1-4}$ alkyl, amino, $C_{1-4}$ alkylamino, di—$C_{1-4}$ alkylamino $C_{5-7}$ cycloalkylamino, $C_{5-7}$ cycloalkyl ( $C_{1-4}$ alkyl) amino. anilino, N—$C_{1-4}$ alkylanilino and groups as defined for Ar above;
or Q is a cyclic moiety selected from 1-hydroxy-1,3-dihydroimidazol-2-one and groups of formula

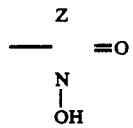

in which Z is a $C_{2-5}$ alkylene chain in which one of the carbon atoms may be replaced by a hetero atom;
and salts thereof;
subject to certain provisos indicated in the Application.
The European application refers to certain prior art related to the claimed subject matter, namely:
(a) Patents:

| | |
|---|---|
| EP 0 161 939 A | |
| GB 1 226 344 | GB 1 427 114 |
| GB 1 278 739 | GB 1 437 783 |
| GB 1 315 830 | GB 1 444 492 |
| GB 1 382 996 | GB 2 047 234 A |
| GB 1 396 726 | |
| US 3 600 437 | US 3 972 934 |
| US 3 821 289 | US 3 978 116 |
| US 3 890 377 | |
| JP 57035543 | JP 57062239 |

(b) Literature references:
Tetrahedron, 1970, 26 (23), 5653–64,
Eur. J. Med. Chem. Chimica. Therapeutica, 1975, 10 (2), 125–128,
Eur. J. Med. Chem. Chimica. Therapeutica, 1970, 13 (2), 211–13,
J. Chem. Eng. Data, 1985, 30, 237–9,
Chem. Biol. Hydroxamic Acids [Proc. Int. Symp.], 1981, 51–62,
Arzneim. Forsch., 1978, 28 (11), 2087–92.
We have now found that within the class of compounds described in European patent application No. 86301895, there is a sub-class of compounds and salts having advantageous pharmacological properties with regard to the inhibition of lipoxygenase and/or cyclooxygenase, particularly in respect of their surprisingly long duration of action.

According to the present invention, therefore, there is provided a compound of formula (II)

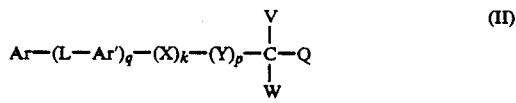

wherein
q is 1, k is 0, and p is 1;
Ar is phenyl optionally substituted by one or more substituents independently selected from $C_{1-4}$ alkyl (which may be substituted by one or more halogen atoms) and halogen;
L is —O—;
Ar' is 1,3- or 1,4-phenylene;
Y is (E)—CH=CH—;
V is hydrogen or $C_{1-4}$ alkyl;
W is $C_{1-4}$ alkyl; and
Q is a moiety of formula

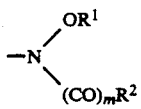

wherein m is 1, $R^1$ is hydrogen, and $R^2$ is hydrogen or $C_{1-4}$ alkyl;
and salts thereof.

Compounds of formula (II) wherein V=W may exist as one of two enantiomeric forms ((R) or (S)) or as a mixture of the two forms in any proportions. Where the absolute chiralities of the enantiomeric forms are unknown, each may be identified in terms of its optical rotation as either the laevorotatory form or the dextrorotatory form. The present invention includes any compound of formula (II) wherein V≠W in either its laevorotatory or dextrorotatory form or as a mixture thereof in any proportions. The invention further includes bioprecursors or "pro-drugs" of the compounds of the invention that is, compounds which are converted in vivo to compounds of formula (II) or their physiologically acceptable salts.

According to further aspects of the invention, there are provided processes for the preparation of compounds of formula (II), pharmaceutical formulations containing them, and uses for them in medicine and in other applications.

For use in medicine, the salts of the compounds of formula (II) are those salts which are physiologically acceptable. However, non-physiologically acceptable salts are included within the ambit of the present invention, either for use in non-medical applications such as further described hereinbelow, or for use as intermediates in the preparation of compounds of formula (II) and their physiologically acceptable salts.

Preferred compounds of the invention having exceptionally desirable pharmacological properties include:
(E)-N-[1-Methyl-3-(3-phenoxyphenyl)prop-2-enyl]acetohydroxamic acid, mp 90°-91° C.;
(E)-N-{1-Methyl-3-[3-(4-methylphenoxy)phenyl]prop-2-enyl}acetohydroxamic acid, mp 90°-92° C.;
(E)-N-{1-Methyl-3-[3-(4-t-butylphenoxy)phenyl]prop-2-enyl}acetohydroxamic acid, 92°-94° C.

(E)-N-{1-Methyl-3-[3-(4-chlorophenoxy)phenyl]prop-2-enyl}acetohydroxamic acid, mp 86°-87° C.;
(E)-N-{1-Methyl-3-[3-(4-bromophenoxy)phenyl]prop-2-enyl}acetohydroxamic acid, mp 93°-95° C.;
(E)-N-{1-Methyl-3-[3-(3-trifluoromethylphenoxy)phenyl]prop-2-enyl}acetohydroxamic acid, mp 83°-85° C.;
(E)-N-{1-Methyl-3-[3-(3,5-dichlorophenoxy)phenyl]prop-2-enyl)acetohydroxamic acid, mp 93°-95° C.;
(E)-N-{1-Methyl-3-[3-(4-fluorophenoxy)phenyl]prop-2-enyl}acetohydroxamic acid, mp 81°-83° C.; and
(E)-N-{1-Methyl-3-[3-(2,4-difluorophenoxy)phenyl]prop-2-enyl)acetohydroxamic acid, mp 79°-81° C.;
in either their (+) or (−) enantiomeric form or as a mixture thereof in any proportions,
and physiologically acceptable salts thereof.

The laevorotatory enantiomers of the preferred compounds are particularly preferred for use in medicine in view of their prolonged duration of action.

Acid addition salts according to the invention include the acetate. adipate, alginate, aspartats, benzoate, benzenesulphonate, bisulphate, butyrate, citrate, camphorate, camphorsulphonate, cyclopentanepropionate, digluconate, dodecylsulphate, ethanesulphonate, fumarate, glucoheptanoate glycerophosphate, hemisulphate, heptanoate, hexanoate, hydrochloride, hydrobromide, hydroiodide, 2-hydroxyethanesulphonate, lactate, maleate, methanesulphonate, 2-naphthalenesulphonate, nicotinate, oxalate, palmonate, pectinate, persulphate, 3-phenylpropionate, picrate, pivalate, proprionate, succinate, tartrate, thiocyanate, tosylate and undeconoate.

Base salts according to the invention include ammonium salts, alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts according to the invention may be prepared when a nitrogen-containing group is present, for example, by reaction with lower alkyl halides, such as methyl, ethyl, propyl, and butyl chlorides, bromides and iodides, with dialkyl sulphates, with long chain halides such as decyl, lauryl, myristyl and stearyl chlorides, bromides and iodides, and with aralkyl halides such as benzyl and phenethyl bromides.

Subject to any limitations expressed or implied herein, the present invention also provides any compound of formula (I). or any physiologically acceptable salt thereof, for use as an inhibitor of the lipoxygenase and/or cyclo-oxygenase enzymes of the mammalian arachidonic acid metabolism, to methods of inhibition of such enzyme(s) by administration to a mammal of a lipoxygenase and/or cyclo-oxygenase (as appropriate) inhibiting amount of any such compound or salt, and to the use of any such compound or salt in the manufacture of lipoxygenase and/or cyclo-oxygenase inhibiting (as appropriate) agents.

Further, and also subject to any limitations expressed or implied herein, the present invention also provides any compound of formula (I), or any physiologically acceptable salt thereof, for use as a medical therapeutic and/or prophylactic agent, to methods of medical therapeutic and/or prophylactic treatment by administration to a mammal of a medically therapeutic and/or prophylactic (as appropriate) effective amount of any such compound or salt, and to the use of any such compound or salt in the manufacture of medically therapeutic and/or prophylactic (as appropriate) agents. The kinds of medical therapy and prophylaxis pertinent to the foregoing are elaborated by way of example in the following paragraphs, but are not intended to be construed as in any way limiting the scope of these aspects of the invention.

By virtue of their lipoxygenase inhibitory properties, said compounds and salts find application in the treatment and/or prophylaxis of any condition where a lipoxygenase inhibitor is indicated, especially spasmogenic and allergic conditions and tumours.

By virtue of their cyclo-oxygenase inhibitory properties, said compounds and salts find application in the treatment and/or prophylaxis of any condition where a cyclo-oxygenase inhibitor is indicated, especially pyresis and pain.

By virtue of both their lipoxygenase and cyclooxygenase inhibitory properties, said compounds and salts find application in the treatment and/or prophylaxis of any condition where a dual lipoxygenase/cyclo-oxygenase inhibitor is indicated, especially any condition involving blood platelet aggregation or inflammation. In the case of inflammation, the compounds and salts of the invention are particularly suited to the treatment and/or prophylaxis of conditions associated with the infiltration of leucocytes into inflamed tissue.

In determining whether a lipoxygenase, cyclo-oxygenase or dual lipoxygenase/cyclo-oxygenase inhibitor is indicated, of course inter alia, the particular condition in question and its severity must be taken into consideration and the determination is ultimately at the discretion of the attendant physician.

Examples of the aforesaid spasmogenic conditions are those involving smooth muscle tissue, especially airway smooth muscle constriction such as intrinsic asthma (including intrinsic or idiopathic bronchial asthma and cardiac asthma), bronchitis and arterial smooth muscle constriction such as coronary spasm (including that associated with myocardial infarction, which may or may not lead to left ventricular failure resulting in cardiac asthma) and cerebral spasm or 'stroke'. Other examples include bowel disease caused by abnormal colonic muscular contraction such as the conditions termed 'irritable bowel syndrome', 'spastic colon' and 'mucous colitis'.

Examples of the aforesaid allergic conditions are extrinsic asthma (from which it will be appreciated that the compounds and salts of the invention are particularly favourable as anti-asthmatic agents), allergic skin diseases having a total or partial allergic origin, such as eczema. allergic bowel diseases (including coeliac disease), allergic eye conditions, such as hayfever (which may additionally or alternatively affect the upper respiratory tract), and allergic conjunctivitis.

Examples of the aforesaid tumours are skin neoplasms, both benign and malignant.

Examples of the aforesaid pyretic and painful conditions include fever associated with infections, trauma and injury, malignant disease, and diseases affecting the immune system (including anto-immune diseases).

Example of the aforesaid conditions involving blood platelet aggregation are those resulting from thrombosis, including 'strokes' having a total or partial thrombotic origin, coronary thrombosis, phlebitis and phlebothrombosis (the latter two conditions also possibly being associated with inflammation).

Examples of the aforesaid conditions involving inflammation are inflammatory conditions of the lung, joints, eye, bowel, skin and heart.

Inflammatory lung conditions which may be treated and/or prevented include asthma and bronchitis (vide supra) and cystic fibrosis (which may additionally or alternatively involve the bowel or other tissue(s)).

Inflammatory joint conditions which may be treated and/or prevented include rheumatoid arthritis, rheumatoid spondylitis, osteoarthritis, gouty arthritis and other arthritic conditions.

Inflammatory eye conditions which may be treated and/or prevented include uveitis (including iritis) and conjunctivitis (vide supra).

Inflammatory bowel conditions which may be treated and/or prevented include Crohn's disease, ulcerative colitis and distal proctitis.

Inflammatory skin diseases which may be treated and/or prevented include those associated with cell proliferation, such as psoriasis and eczema (vide supra) and dermatitis (whether or not of allergic origin).

Inflammatory conditions of the heart which may be treated and/or prevented include coronary infarct damage.

Other inflammatory conditions which may be treated and/or prevented include tissue necrosis in chronic inflammation and tissue rejection following transplant surgery.

It is also believed that compounds of formula (II) and their physiologically acceptable salts are effective agents in the prophylaxis and/or treatment of (i) bacterial and fungal infections and (ii) dysmenorrhoea, these applications forming further aspects of the present invention.

It is known from the literature that some compounds which are cyclo-oxygenase and/or lipoxygenase inhibitors can delay the decay of cut plant matter. Thus it is believed that by virtue of their enzyme inhibitory effects, compounds of formula (II) and their salts are also useful for controlling the processes of growth and decay in plants. Therefore the present invention also provides compounds of formula (II) and their salts for use in a method of regulating the growth of, or delaying senescence in, vegetable matter by application to said matter of an effective amount of a compound of formula (II) or a salt thereof.

The term "senescence" refers to the process whereby plant matter decays, especially after being picked, cut or otherwise removed from its normal growing environment. Vegetable matter includes trees, shrubs, flowers, edible vegetables and other food crops.

The above method is particularly applicable to flowers intended for decorative or display purposes such as carnations, crysanthemums, daisies, begonias, etc. These include perennial annual and biannual flowers, for example, those that grow from bulbs (e.g. dahlias) or from seed (e.g. marigolds). The method is also especially suitable for use with decorative shrubs and trees, for example, those which are displayed when cut, such as Christmas trees.

Compounds of formula (II) and their salts may also be used for the preservation of picked fruits.

For medical use, the amount required of a compound of formula (II) or a physiologically acceptable salt thereof (hereinafter referred to as the active ingredient) to achieve a therapeutic effect will, of course, vary with the particular compound, the route of administration, the mammal under treatment, and the particular disorder or disease being treated. A suitable dose of a compound of formula (II) or of a physiologically acceptable salt thereof for a mammal suffering from, or likely to suffer from, any condition as described hereinbefore is 0.1 μg–500 mg of base per kilogram bodyweight. In the case of systemic administration, the dose is typically in the range 0.5 to 500 mg of base per kilogram bodyweight, the most preferred dosage being 0.5 to 50 mg/kg bodyweight, for example, 5 to 25 mg/kg, administered two or three times daily. In the case of topical administration, e.g. to the skin or eye, a suitable dose is in the range 0.1 ng–100 μg of base per kilogram, typically about 0.1 μg/kg.

In the case of oral dosing for the treatment or prophylaxis of airway smooth muscle constriction, or asthma or bronchitis in general, due to any cause, a suitable dose of a compound of formula (II) or of a physiologically acceptable salt thereof may be as specified in the preceding paragraph, but most preferably is from 1 mg to 10 mg of base per kilogram bodyweight the most preferred dosage being from 1 mg to 5 mg/kg bodyweight, for example, from 1 to 2 mg/kg. In the case of pulmonary administration for the latter indications, the dose is typically in the range 2 μg to 100 mg/kg, for example, from 20 μg to 0.5 mg/kg, especially from 0.1 to 0.5 mg/kg.

While it is possible for the active ingredient to be administered alone, it is preferable to present it as a pharmaceutical formulation comprising a compound of formula (II) or a pharmacologically acceptable salt thereof and a physiologically acceptable carrier therefor. Such formulations constitute a further feature of the present invention. Generally, the active ingredient comprises from 0.1% to 99.9% by weight of the formulation. Typically, unit doses of a formulation according to the invention contain from 0.1 mg to 1 g of the active ingredient. For topical administration, the active ingredient preferably constitutes from 1% to 2% by weight of the formulation, but the active ingredient may constitute as much as 10% w/w. Formulations suitable for nasal or buccal administration (such as the self-propelling powder dispensing formulations described below), typically comprise from 0.1 to 20% w/w. for example, 2% w/w of active ingredient.

The formulations of the present invention, both for veterinary and human medical use, comprise an active ingredient in association with a pharmaceutically acceptable carrier therefor and optionally other therapeutic ingredient(s). The carrier(s) must be acceptable in the sense of being compatible with the other ingredients of the formulation and must not be detrimental to the recipient.

Formulations according to the invention include those in a form suitable for oral, pulmonary, ophthalmic, rectal, parenteral (including subcutaneous, intramuscular and intravenous), intra-articular, topical, nasal, or buccal administration.

The formulations of the invention may conveniently be presented in unit dosage form and may be prepared by any method well known in the art of pharmacy. All such methods include the step of bringing the active ingredient into association with a carrier which constitutes one or more accessory ingredients. In general, the formulations are prepared by uniformly and intimately bringing the active ingredient into association with a liquid carrier or a finely divided solid carrier, or both, and then, if desired, shaping the product into the required form.

Formulations according to the present invention which are suitable for oral administration may be in the form of discrete units such as capsules, cachets, tablets, or lozenges, each containing a predetermined amount of the active ingredient; in the form of a powder or granules; in the form of a solution or a suspension in an aqueous or non-aqueous liquid; or in the form of an oil-in-water or water-in-oil emulsion. The active ingredient may also be in the form of a bolus, electuary, or paste.

A tablet may be made by compressing or moulding the active ingredient, optionally with one or more accessory ingredients. Compressed tablets may be prepared by compressing, in a suitable machine, the active ingredient in a free-flowing form such as a powder or granules, optionally mixed with a binder, lubricant, inert diluent, and/or surface active or dispersing agent. Moulded tablets may be made by moulding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration typically comprise a sterile aqueous preparation of the active ingredient which is preferably isotonic with the blood of the recipient.

Formulations suitable for intra-articular administration may be in the form of a sterile aqueous preparation of the active ingredient, which latter may be in microcrystalline form, for example, an aqueous microcrystalline suspension. Liposomal formulations and biodegradable polymer systems may also be used to present the active ingredient for both intra-articular and ophthalmic administration.

Formulations suitable for topical administration include liquid and semi-liquid preparations such as liniments, lotions and applications; oil-in-water and water-in-oil emulsions such as creams, ointments and pastes; and solutions and suspensions such as drops. For example, for ophthalmic administration, the active ingredient may be presented as aqueous eye drops, for example, in the form of a 0.1–1.0% solution.

Formulations suitable for administration to the nose or buccal cavity include powder and self-propelling spray formulations such as aerosols and atomisers. The formulations, when dispersed, preferably have a particle size in the range 0.1 to 200 μm.

A particularly desirable formulation of the present invention for use in the prophylaxis or treatment of airway smooth muscle constriction due to any cause, for example, asthma or bronchitis, is one suitable for pulmonary administration via the buccal cavity. Preferably the formulation is such that particles having a diameter of from 0.5 to 7 μm, most preferably from 1 to 6 μ. which contain active ingredient are delivered directly into the lungs of a patient. Such formulations are conveniently in the form of dry powders for administration from a powder inhalation device or a self-propelling powder-dispensing container, for example, a self-propelling aerosol formulation in a sealed container. Preferably the powders comprise particles containing active ingredient of which at least 98% by weight have a diameter of greater than 0.5 μm and at least 95% by number have a diameter of less than 7 μm. Most preferably at least 95% by weight of the particles have a diameter of greater than 1 μm and at least 90% by number have a diameter of less than 6 μm.

Formulations according to the invention in the form of a dry powder preferably include a solid fine powder diluent such as sugar and are typically presented in a pierceable capsule made, for example, of gelatin.

Self-propelling formulations according to the invention may be either powder-dispensing formulations or formulations dispensing the active ingredient in the form of droplets of a solution or suspension. Self-propelling powder-dispensing formulations typically comprise a liquid propellant having a boiling point of less than 18° C. at atmospheric pressure. Generally, the propellant constitutes from 50 to 99.9% w/w of the composition and the active ingredient constitutes from 0.1 to 20% w/w, for example, about 2% w/w. The carrier in such formulations may include other constituents, for example, a liquid non-ionic or solid anionic surfactant or a solid diluent (preferably having a particle size of the same order as the particles of active ingredient), or both. The surfactant generally constitutes from 0.01 to 20% w/w of the formulation, though preferably less than 1% w/w.

Self-propelling formulations of the invention wherein the active ingredient is present in solution typically comprise an active ingredient, propellant. co-solvent(s), and, advantageously, an antioxidant stabiliser. The co-solvent(s) generally constitutes from 5 to 40% w/w of the formulation, though preferably less than 20% w/w.

Formulations according to the invention may also be in the form of an optionally sterile aqueous or dilute alcoholic solution of the active ingredient for use in a nebuliser or atomiser, wherein an accelerated air stream is used to produce a fine mist consisting of small droplets of the solution. Such formulations typically contain a flavouring agent, such as saccharin sodium, and a volatile oil. A buffering agent and a surface active agent may also be incorporated in such a formulation, which may further contain a preservative such as methyl hydroxybenzoate.

Other formulations of the invention suitable for nasal administration include a coarse powder having a particle size of from 20 to 500 μm which is administered in the manner in which snuff is taken, i.e. by rapid inhalation through the nasal passage from a container of the powder held close to the nose.

In addition to the aforementioned ingredients, the formulations of the invention may include one or more additional ingredients such as diluents, buffers, flavouring agents, binders, surface active agents, thickeners, lubricants, preservatives (including anti-oxidants e.g. methyl hydroxybenzoate), emulsifying agents and the like. Any other therapeutic ingredient may comprise one or more of an antibiotic (e.g. anti-bacterial). anti-fungal or anti-viral agent, or an anti-histamine (particularly a peripherally-acting anti-histamine). However, according to another aspect of the invention, when such other agent(s) is also present, the compound of formula (II), or a physiologically acceptable salt thereof, and the other agent(s) need not necessarily be present as a pharmaceutical formulation as hereinbefore defined, but may merely be in combination or intimate admixture, i.e. a pharmaceutically acceptable carrier need not be present.

The combination with an anti-histamine is particularly favoured for anti-asthmatic use. Such an anti-histamine may be selected from any compound described in European patent applications Nos. 859959 A and 117302 A. The amount and dosage regime for such an anti-histamine may be chosen from any of those recited in these two patents. Especially preferred are the anti-histamines (E)-3-(6-(3-pyrrolidino-1-(4-tolyl)prop-1E-enyl-(2-pyridyl)acrylic acid and (E)-3-(6-(3-pyrrolidino-1-(4-tolyl) prop-1E-enyl-(2-pyridyl)propionic acid. Another preferred anti-histamine is (E)-1-(4-methylphenyl)-1-(2-pyridyl)-3-pyrrolidinoprop-1-ene, otherwise known as triprolidine.

For delaying senescence of cut or picked matter, or for controlling plant growth, the compounds of formula (II) and their salts are preferably presented in a suitable formulation optionally containing one or more other agents for enhancing the freshness of the plants. Such compositions include solutions and suspensions of the compound in a suitable medium such as an aqueous medium.

The formulations of the invention may be applied by immersing part (e.g. the cut end) or all of the cut or picked plant in the formulation by spraying the plant with the formulation before or after cutting or picking, or by applying the formulation to the root structure before or after cutting or picking. Thus the formulation may be applied to the root structure while the plant is still in the ground by spreading the formulation on the soil around the plant from where it is conveyed to the roots by rainwater or other watering means. When applied in aqueous solution, the compounds of the invention may be presented in a concentration of from 1 μM to 1 M. for example, from 100 μM to 100 μM. A typical concentration is about 1 mM.

The compounds of formula (II) and their salts may be prepared by any of the following processes (subject to any limitations expressed therein) which constitute further aspects of the invention:

(a) reacting a compound of formula (III)

$$R^9N(OZ^1)H \qquad (III)$$

(wherein $R^9$ is a group of formula

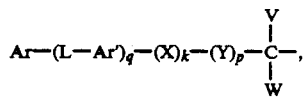

as hereinbefore defined, and $Z^1$ is hydrogen or a suitable protecting group) with an acylating agent, and, when $Z^1$ is a protecting group, subjecting the product to such conditions and/or reacting it with one or more reagents as appropriate to effect removal of said protecting group;

(b) reacting a compound of formula (IV)

$$R^6 NHOH \qquad (IV)$$

with a compound of formula (V)

$$R^7-R^8 \qquad (V)$$

wherein $R^6$ is $-(CO)_m R^2$, as hereinbefore defined, $R^7$ is a group of formula

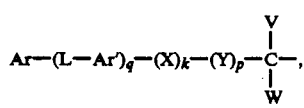

as hereinbefore defined, and $R^8$ is a suitable leaving group;

(c) treating a compound of formula (VI)

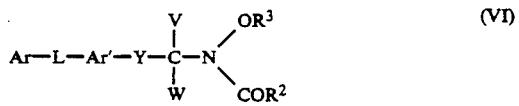

wherein Ar, L, Ar', Y, V, W and $R^2$ are as hereinbefore defined and $R^3$ is a hydrolytically cleavable group, such as alkoyl or aroyl, for example, benzoyl, with a suitable base, such as potassium carbonate; or (d) partially reducing a compound of formula (VII)

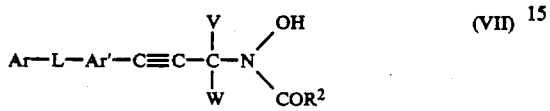

wherein Ar, L, Ar', V, W and $R^2$ are as hereinbefore defined, for example, by quantitative hydrogenation over a suitable catalyst such as Lindlar. Catalytic hydrogenation is particularly preferred to achieve stereospecific reduction of the triple bond to give the desired (E)-form of the group Y;

and optionally converting the compound of formula (II) so formed to a corresponding salt thereof.

In optional process (a). compounds of formula (III) wherein $Z^1$ is hydrogen may be prepared by oximation of the corresponding ketone using, for example, hydroxylamine in a suitable polar solvent such a methanol. The ketone may be obtained commercially or by reaction of the corresponding aldehyde with, for example, aqu. NaOH/acetone or dimethyl acetylmethyl. phosphonate and anhy. $K_2CO_3$ in a suitable solvent such as THF.

When optional process (a) is used to prepare a compound of formula (II) (regardless of whether $Z^1$ in compound (III) is hydrogen or a protecting group), the acylating agent is typically an appropriate anhydride or activated acid, such as an acid halide, for example, acetyl chloride.

Where the group $Z^1$ in the compound of formula (III) is a protecting group, this may, for example, be selected from acetyl, benzyl, O-benzyl, trityl, tetrahydropyranyl, O-tetrahydropyranyl, O-t-butyl and benzoyl. The protecting group may be removed by treatment with acid or base or by hydrogenation by methods readily apparent to those skilled in the art. In general, suitable protecting groups and methods for their removal will be found in T.W. Greene, Protective Groups in Organic Synthesis, Wiley, N.Y., 1981. Particular examples of removal of such leaving groups include removal of the O-benzyl group by hydrogenolysis over 5% palladium charcoal at room temperature and removal of the O-tetrahydropyranyl group using pyridinium para-toluene sulphate in refluxing methanol.

In optional process (b), compounds of formula (IV) may be prepared by the reduction of compounds of formula (III) wherein $Z^1$ is hydrogen using, for example, sodium cyanoborohydride either in glac. acetic acid or in the presence of oxalic acid in a suitable polar solvent such as methanol.

Alternatively, compounds of formula (IV) may be prepared by acid hydrolysis of the corresponding —N(BOC)OBOC compound, which may itself be prepared by treating the appropriate alcohol (A) with HN(BOC)OBOC in the presence of triphenylphosphine/DEAD or by reacting a compound of formula (XIV) (vide infra) wherein V and W are as defined and $R^2$ and $R^3$ are both t-butoxy groups with a compound of formula (XV) (vide infra) wherein Ar, Ar', L and T are as defined. The compound of formula (XIV) may be obtained by treatment of the corresponding alcohol (B) with HN(BOC)OBOC in the presence of triphenylphosphine/DEAD or by partial reduction of the corresponding alkyne. The alkyne may be obtained by treatment of the corresponding alcohol (C) with HN(BOC)OBOC in the presence of triphenylphosphine/DEAD. The alcohols A, B and C may be obtained commercially or by reduction of the appropriate ketones using, for example, sodium borohydride in methanol.

When optional process (b) is used to prepare a compound of formula (II), the compound of formula (IV) may be used in the form of a salt thereof and the compound of formula (V) is typically an appropriate anhydride or activated acid, such as an acid halide, for example, acetyl chloride. Preferably, the reaction is effected in a suitable solvent and, where the compound of formula (IV) is in the form of a salt, in the presence of a base, such as an appropriate amine, so that the free hydroxylamine compound is liberated in situ.

In optional process (c). compounds of formula (VI) may be prepared by partially reducing the corresponding alkyne, for example, by quantitative hydrogenation over a suitable catalyst such as Lindlar. Catalytic hydrogenation particularly preferred to achieve stereospecific reduction of the triple bond to give the desired (E)-form of the group Y.

The appropriate alkynes may be prepared by reacting a compound of formula (VIII)

wherein Z, V, W, $R^2$ and $R^3$ are as hereinbefore defined, with a compound of formula (IX)

wherein Ar, L and Ar' are as hereinbefore defined and T is a suitable leaving group, such as bromo or iodo, typically in the presence of bis-triphenylphosphonium palladium dichloride and a suitable base, such as triethylamine, followed by treatment with copper(I) iodide.

Compounds of formula (VIII) may be prepared by reacting a compound of formula (X)

wherein V, W, and $R^3$ are as hereinbefore defined, with a compound of formula (XI)

wherein $R^2$ is as hereinbefore defined and T is a suitable leaving group such as chloro, typically in the presence of a suitable base for example, pyridine.

Compounds of formula (X) may be prepared by reacting a compound of formula (XII)

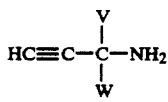 (XII)

wherein V and W are as hereinbefore defined, with a compound of formula (XIII)

 (XIII)

wherein R³ is as hereinbefore defined and T is a suitable leaving group, for example, —OR³.

The compounds of formulae (IX) (XI) and (XIII) are commercially available or may be prepared by methods described in the chemical literature.

Alternatively, compounds of formula (VI) may be prepared by reacting a compound of formula (XIV)

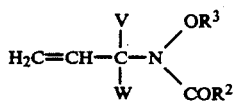 (XIV)

wherein V, W, R² and R³ are as hereinbefore defined, with a compound of formula (XV)

 (XV)

wherein Ar, Ar', and L are as hereinbefore defined and T is a suitable leaving group, such as bromo, typically at an elevated temperature in the presence of Pd(OAc)₂, tri-o-tolylphosphine and a suitable base, for example, triethylamine.

Compounds of formula (XIV) may be prepared by partially reducing the corresponding alkyne, for example, by quantitative hydrogenation over a suitable catalyst such as Lindlar. The appropriate alkynes and compounds of formula (XV) are available commercially or may be prepared by methods described in the literature.

In optional process (d), compounds of formula (VII) may be prepared by hydrolysis of a corresponding alkyl or aryl ester using, for example, a suitable base, such as anhy K₂CO₃, in a polar solvent such as methanol.

The appropriate esters may be prepared by reacting compounds of formulae (VIII) and (IX) as described above.

The individual enantiomers of a compound of formula (II) wherein V≠W may be obtained by separation of the components of the racemic mixture, for example, by means of a chiral chromatography column or by preparing and separating suitable diastereoisomers, or by chiral synthesis of each enantiomer.

Chiral syntheses of compounds of formula (II) wherein V≠W may conveniently be carried out by process (b) in which the compound of formula (IV) used therein is derived from the corresponding chiral —N(BOC)OBOC compound. The chiral —N(BOC)OBOC compound may be obtained by treating the appropriate chiral alcohol (A) with HN(BOC)OBOC in the presence of triphenylphosphine/DEAD or by reacting the corresponding chiral compound of formula (XIV) wherein V and W are as defined and R² and R³ are both t-butoxy groups with a compound of formula (XV) wherein Ar, Ar', L and T are as defined. The chiral compound of formula (XIV) may be obtained by treatment of the appropriate chiral alcohol (B) with HN(BOC)OBOC in the presence of triphenylphosphine/DEAD or by partial reduction of the corresponding chiral alkyne. The chiral alkyne may be obtained by treatment of the corresponding chiral alcohol (C) with HN(BOC)OBOC in the presence of triphenylphosphine/DEAD. The appropriate chiral alcohols A. B and C may be obtained commercially or prepared from the corresponding ketones by means of suitable chiral reducing agents (JACS 109, 7925 (1987)). Alternatively, the achiral alcohols may be derivatised and selectively hydrolysed to the desired enantiomers (JCS Chem. Comm. 598 (1988)). The chiral —N(BOC)OBOC compound may be converted to the corresponding chiral compound of formula (IV) by, for example, acid hydrolysis. The chiral compound of formula (IV) is then converted to the chiral product of formula (II) by process (b).

Optional conversion of a compound of formula (II) to a corresponding salt may conveniently be effected by reaction with an appropriate organic or mineral acid, or with a base.

For a better understanding of the invention, the following Examples are given by way of illustration. In the Examples and elsewhere in the specification, the following abbreviations are used:

| AIBN | Azoisobutyronitrile |
| --- | --- |
| -BOC | t-butoxycarbonyl |
| DCC | 1,3-Dicyclohexylcarbodiimide |
| DEAD | Diethyl azodicarboxylate |
| DMAP | 4-Dimethylaminopyridine |
| NBS | N-Bromosuccinimide |
| TDA-1 | Tris(3,6-dioxaheptyl)amine | all of which are available from Aldrich Chemical Company Ltd.

EXAMPLES

SYNTHETIC EXAMPLE 1

Preparation of (E)-N-[1-methyl-3-(3-phenoxyphenyl)prop-2-enyl-]acetohydroxamic acid (a) (E)-1-(3-Phenoxyphenyl)buten-3-one 6.7% w/v aqu. NaOH (12 ml) was added to a solution of 3-phenoxybenzaldehyde (40 g, Aldrich) in acetone (200 ml). The mixture was stirred for ½ hour and then poured into 2 M aqu. HCl and extracted with ether/pet.ether (1:1). The extract was washed with satd. aqu. NaCl, dried over MgSO4 and stripped to give the aldol product. The latter was taken up in toluene (100 ml) p-toluenesulphonic acid (1 g) was added and the mixture heated on a steam-bath for 1 hour. The mixture was then cooled, washed with satd. aqu. NaHCO₃ and satd. aqu. NaCl. dried over MgSO4, and stripped to give the desired product (39.0 g).

(b) (E)-1-(3-Phenoxyphenyl)buten-3-one oxime

The product from step (a) (10.0 g) and hydroxylamine hydrochloride (7 g) were taken up in methanol (50 ml), pyridine (15 ml) was added and the mixture stirred for 1 hour. The mixture was then stripped, redissolved in ether, washed with 2N aqu. HCl and satd. aqu. NaCl, dried over MgSO4, and stripped to give the desired product (10.2 g).

(c) (E)-N-[1-Methyl-3-(phenoxyphenyl)prop-2-enyl]acetohydroxamic acid

The product from step (b) (7.0 g) was taken up in glac. acetic acid (50 ml), sodium cyanoborohydride (2 g) was added and the mixture stirred at room temperature for 2 hours. A further portion of sodium cyanoborohydride (0.75 g) was then added and the mixture stirred at room temperature for a further 2 hours. Acetic anhydride (10 ml) was then added and the mixture stirred for ¾ hour. The mixture was then stripped and the residue redissolved in ether, washed with water, satd. aqu. NaHCO$_3$ and satd. aqu. NaCl, dried over MgSO$_4$ and stripped to give the N,N-diacetyl derivative. The latter was taken up in methanol (60 ml), anhy. potassium carbonate (3 g) was added, and the mixture stirred for ½ hour. Water was then added, followed by 40% w/v aqu. NaOH (10 ml). The mixture was washed with ether, poured into 2 M HCl and extracted with ether. The extract was washed with satd. aqu. NaCl, dried over MgSO$_4$ and stripped, and the residue recrystallised from ether/pet.ether (1:1) to give the desired product (2.1 g), mp 90°-90° C.

(d) Optional enantiomeric separation of (±)-(E)-N-[1-methyl-3-(3-phenoxyphenyl)prop-2-enyl]acetohydroxamic acid For the separation, a Chiracel Type OB chiral HPLC column (Daicel Chemical Industries Ltd) equipped with a 254 nm UV detector was used in which the mobile phase was methanol/water/acetic acid (65:35:0.1) containing oxalic acid at a concentration of 0.5 mM. A 1 mg/ml solution of the product from step (c) was prepared in the mobile phase mixture and a 5 µl aliquot injected on to the column. The two enantiomers were separated with retention times of 37 minutes (Isomer I, laevorotatory) and 43 minutes (Isomer II, dextrorotatory).

SYNTHETIC EXAMPLE 2

Preparation of (+)-(E)-N-[1-methyl-3-(3-phenoxyphenyl)prop-2-enyl]acetohydroxamic acid and (−)-(E)-N-[1-methyl-3-(3-phenoxyphenyl)prop-2-enyl]acetohydroxamic acid

(a) (E)-1-(3-Phenoxyphenyl)buten-3-one

By the method of Synthetic Example 1, step (a).

(b) (±) (E)-1-(3-Phenoxyphenyl)but-1-en-3-ol

The product from step (a) (11.9 g) was taken up in methanol (100 ml) and cooled to −78° C. Sodium borohydride was added and the mixture stirred for 3 hours. A further portion of NaBH$_4$ (2 g) was then added and the mixture stirred for a further 5 hours, then allowed to warm to room termpperature. After standing overnight, the mixture was stripped, the residue partitioned between ether and water (150 ml of each), and the organic phase separated, washed with satd. aqu. NaCl, dried over MgSO$_4$, and stripped to give the desired product (12.01 g).

(c) (±)-(E)-1-(3-Phenoxyphenyl)but-1-en-3-yl chloroacetate

The product from step (b) (12.01 g) and chloroacetic acid (5 g) were taken up in methylene chloride, DCC (15 g) was added, and the mixture stirred for 5 minutes. DMAP (0.5 g) was then added, causing the mixture to boil, and the mixture stirred for 1 hour. Ether (200 ml) was then added, the mixture filtered, and the filtrate washed with satd. aqu. NaHCO$_3$, 2 M aqu. HCl, and satd. aqu. NaCl, dried over MgSO$_4$ and stripped. The residue was taken up in ether/pet.ether (1:1, 100 ml), filtered, and stripped to give the desired product (15.7 g).

(d) (+)-(E)-1-(3-Phenoxyphenyl)but-1-en-3-ol and (−)-(E)-1-(3-Phenoxyphenyl) but-1-en-3-ol The product from step (c) (9.5 g) was taken up in 0.1 M aqu. phosphate buffer (250 ml, pH 7) under N$_2$ and lipase (150 mg, Fluka Cat. No. 62312) was added. As the reaction proceeded, 1 M aqu. NaOH was added from an autoburette to maintain the pH at 7 (14.5 ml added over 27 hours). After 27 hours, methylene chloride (250 ml) was added, the mixture dried over MgSO$_4$ and stripped, and the residue eluted through a silica gel column using ether. The eluate was monitored by TLC and similar fractions combined and stripped to give (+)-(E)-1-(3-phenoxyphenyl) but-1-en-3-ol (3.7 g, $[\alpha]_D^{20}$ +8.47° (c.2.72, EtOH)) and chiral (E)-1-(3-phenoxyphenyl)but-1-en-3-yl chloroacetate (3.7 g). The latter compound was taken up in methanol (50 ml), anhy. potassium carbonate (1 g) was added, and the mixture stirred for ½ hour. The mixture was then stripped, the residue partitioned between ether and water, and the organic phase separated, washed with satd. aqu. NaCl, and stripped to give (−)-(E)-1-(3-phenoxyphenyl)but-1-en-3-ol (2.7 g. $[\alpha]_D^{20}$ −11.0° (c.2.92, EtOH)).

(e) Chiral N,O-bis(t-butoxycarbonyl)-N-[1-methyl-3-(3-phenoxyphenyl)prop -2-en-1-yl]hydroxylamine (−)-(E)-1-3(-Phenoxyphenyl)but-1-en-3-ol from step (d) (2.6 g), N,O-bis(t-butoxycarbonyl)hydroxylamine (2.65 g), and triphenylphosphine (4.25 g) were taken up in toluene (30 ml) and cooled to −78° C. under N$_2$. A solution of DEAD (2.9 g) in toluene (10 ml) was then added and the mixture allowed to warm to room tempterature. 40/60 pet.ether (60 ml) was added to precipitate Ph$_3$P=O as a dark gummy mass. The mother liquor was decanted off and stripped to give a tan/orange oil which was eluted through a silica gel column using methylene chloride. The eluate was stripped to give a pale yellow oil which was eluted through a second silica gel column using ether/methylene chloride/40–60 pet.ether (1:1:8) and the eluate stripped to give the desired product as a colourless oil which was dried under high vacuum. Yield 1 97 g.

(f) (+)-(E)-N-[1-methyl-3-(3-phenoxyphenyl)prop-2-enyl]acetohydroxamic acid (Isomer II)

The product from step (e) (1.97 g) was taken up in methylene chloride (12 ml) and trifluoroacetic acid (3 ml) was added under N$_2$. The mixture was stirred for 1 hour at room temperature and then stripped to give the hydroxylamine as a viscous tan/red oil which was taken up in methylene chloride (5 ml).

A solution of pyridine (5 ml) in methylene chloride (10 ml) was cooled to −10° C. under N and acetyl chloride (2 ml) was added over 2 minutes. The solution of tan/red oil was then added and the mixture stirred for 1 hour at 0° C., then poured into a 20% w/v aqu. solution of citric acid (100 ml) and extracted with ether (3×100 ml). The combined extracts were washed with satd. aqu. NaHCO$_3$ (50 ml) and with water (2×500 ml).

dried over Na₂SO₄, and stripped to give a pale yellow gum. The latter was taken up in methanol (25 ml), anhy. potassium carbonate (1.19 g) was added, and the mixture stirred for ½ hour. The mixture was then stripped, the residue partitioned between ether (100 ml) and water (100 ml). and the organic phase separated and extracted with 1 M aqu. NaOH (100 ml). The basic solution was acidified with excess citric acid and extracted with ether (2×100 ml). The combined extracts were washed with water (100 ml), dried over Na₂SO₄, and stripped to give a tan gum which was triturated with EtOAc/40–60 pet.ether (1:2) to induce partial crystallisation and the resulting solid filtered off, recrystallised from EtOAc/40–60 pet.ether (1:2), and dried under vacuum to give a pale cream solid (0.17 g). mp 83°–85° C., $[\alpha]_D^{20}$ +1.3° (essentially racemic material).

The filtrate from the original crystallisation was stripped the residue eluted through a silica gel column using ether, and the eluate stripped to give the desired product as a pale yellow gum which was dried under high vacuum. Yield 0.32 g, $[\alpha]_D^{20}$ +94.8° (c.1.00 EtOH). Analysis of the product by chiral HPLC using the method of Synthetic Example 1, step (d), indicated an enantiomeric excess of 90% (Isomer II:Isomer I, 95:5).

By steps analogues to steps (e) and (f) above, (+)-(E)-1-(3-phenoxyphenyl) but-1-en-3-ol from step (d) was converted to (−)-(E)-N-[1-methyl-3-(3-phenoxyphenyl)prop-2-enyl]acetohydroxamic acid (Isomer I). $[\alpha]_D^{20}$ −98.7°, enantiomeric excess 96% (Isomer I:Isomer II, 98:2).

SYNTHETIC EXAMPLE 3

Preparation of (E)-N-{1-methyl-3-[3-(4-chlorophenoxy)phenyl]prop-2-enyl}acetohydroxamic acid (a) (E)-1-[3-(4-Chlorophenoxy)phenyl]buten-3-one 10 N aqu. NaOH (2 ml) was added to a solution of 3-(4-chlorophenoxy)-benzaldehyde (23.3 g, Aldrich) in acetone (150 ml) and stirred vigorously. After a few minutes' stirring, the temperature rose to 32° C. The mixture was left for 5 minutes and then poured into 2 M aqu. HCl (600 ml) and extracted with ether/pet. ether (1:1, 200 ml). The extract was washed with water and satd. aqu. NaCl, dried over MgSO₄, and stripped to give the aldol product. The latter was taken up in toluene (300 ml), p-toluenesulphonic acid (1 g) was added, and the mixture heated for 1 hour. The mixture was then cooled, washed with satd. aqu. NaHCO₃ and satd. aqu. NaCl, dried over MgSO₄ and stripped. The residue was eluted through a slice gel column using methylene chloride/40–60 pet. ether (1:1, followed by 3:1) and the eluate stripped to give the desired product (19 g).

(b) (E)-1-[3-(4-Chlorophenoxy)phenyl]buten-3-one oxime

The product from step (a) (19 g) and hydroxylamine hydrochloride (6.9 g) were taken up in methanol (100 ml), pyridine (20 ml) was added and the mixture stirred for 1 hour. The mixture was then stripped, redissolved in ether (200 ml), washed with 2 N aqu. HCl and satd. aqu. NaCl, dried over MgSO₄, and stripped to give the desired product (20.3 g).

(c) (E)-N-{1-Methyl-3-[3-(4-chlorophenoxy)phenyl]prop-2-enyl}acetohydroxamic acid The product from step (b) (20 g) was taken up in glac. acetic acid (100 ml), sodium cyanoborohydride (22 g) was added in portions under N₂ over 1.5 hours, and the mixture stirred for a further 1.5 hours. A further portion of sodium cyanoborohydride (2 g) was then added and the mixture stirred for a further ½ hour. Acetic anhydride (25 ml) was then added and the mixture stirred for 1 hour. The mixture was then stripped and the residue redissolved in ether (300 ml), washed with water (2×250 ml), with satd. aqu. NaHCO₃, and with satd. aqu. NaCl, dried over MgSO₄, and stripped to give the N,N-diacetyl derivative. The latter was taken up in methanol (100 ml), anhy. potassium carbonate (10 g) was added, and the mixture stirred for ½ hour. The mixture was then stripped and the residue taken up in 2 M aqu. NaOH (250 ml) and washed with ether (2×250 ml). The basic solution was cooled in ice. its pH adjusted to 3.0 using conc. HCl, and extracted with ether (400 ml). The extract was washed with satd. aqu. NaCl, dried over MgSO₄, and stripped to give the desired product (13 g) which was recrystallised from ether/40–60 pet.ether. Yield 7.4 g, mp 86°–87°.

SYNTHETIC EXAMPLE 4

Preparation of (E)-N-{1-methyl-3-[3-(4-fluorophenoxy)phenyl]prop-2-enyl}acetohydroxamic acid (a) 3-(4-Fluorophenoxy)toluene Sodium hydride (1 80 g) was suspended in 3-bromotoluene (51.3 g, Aldrich) and 4-fluorophenol (8.40 g, Aldrich) added over ¼ hour with stirring. The mixture was then heated at 45° C. until effervescence stopped (½ hour). After cooling, copper(I) chloride (3.75 g) was added followed by TDA-1 (12 g) over 10 minutes with further cooling. The mixture was then heated at 180° C. under N₂ for 24 hours. After cooling, the mixture was treated with 2 M aqu. HCl (100 ml) and extracted with ether. The extract was washed with 2 M aqu. HCl (2×100 ml), with 2 M aqu. NaOH and with water (2×100 ml), then treated with charcoal, filtered through Hyflo and stripped. The residue was distilled under reduced pressure to give the desired product, bp 130°–135° C./10 mm Hg.

(b) 1-Dibromomethyl-3-(4-fluorophenoxy)benzene

A mixture of the product of step (a) (9.0 g) and NBS (17.45 g) in carbon tetrachloride (100 ml) was refluxed for 3 hours in the presence of a UV lamp. The mixture was treated with AIBN (50 mg) at the start of reflux and ½ hour and 1.5 hours thereafter. The mixture was then cooled, further NBS (2.44 g) and AIBN (50 mg) was added, and the mixture heated and irradiated for a further 1.5 hours. The mixture was then cooled and filtered, the residue washed with CCl₄, and the filtrate and washings combined and stripped to give an orange/tan oil which was dried under high vacuum to give the desired product (17.97 g).

(c) 3-(4-Fluorophenoxy)benzaldehyde

A solution of the product of step (b) (16.04 g) in a mixture of ethanol (100 ml) and water (25 ml) was treated with precipitated calcium carbonate (13.37 g) and the mixture refluxed for 20 hours. After cooling, the mixture was filtered, the filtrate stripped, and the residue taken up in 2 M aqu. HCl (100 ml) and extracted with ether (200 ml). The extract was washed with water (100 ml), dried over Na₂SO₄ and stripped to give a pale yellow oil which was distilled under reduced pressure to give the desired product (8.90 g), bp 100°–130° C./0.2 mm Hg.

(d) (E)-1-[3-(4-Fluorophenoxy)phenyl]buten-3-one

A mixture of the product from step (c) (8.9 g). dimethyl acetylmethylphosphonate (6.84 g), anhy. potassium carbonate (11.37 g) and dry THF (100 ml) was heated under N₂ at 50°–55° C. for 20 hours. The mixture was then cooled and filtered, the residue washed with THF, and the filtrate and washings combined and stripped to give a pale orange oil which was eluted through a silica gel column using ether/40–60 pet. ether (1:2) and the eluate stripped and dried under high vacuum to give the desired product as a very pale yellow, viscous oil (5.59 g).

(e) (E)-[3-(4-Fluorophenoxy)phenyl]buten-3-one oxime

The product from step (d) (5.59 g) and hydroxylamine hydrochloride (2.28 g) were taken up in methanol (75 ml), pyridine (5.28 ml) was added over ½ hour, and the mixture stirred for a further ¼ hour. The mixture was then stripped, redissolved in ether, washed with 2 M aqu. HCl (2×100 ml) and with water (200 ml), dried over Na₂SO₄, stripped and dried under high vacuum to give the desired product as a very pale yellow, viscous oil which partially crystallised on standing (5.97 g).

(f) (E)-N-{1-[3-(4-Fluorophenoxy)phenyl]but-1-en-3-yl}hydroxylamine

The product from step (a) (5.92 g) and anhy. oxalic acid (9.83 g) were taken up in methanol (50 ml), sodium cyanoborohydride (2.74 g) was added under N₂ over 1 hour, and the mixture stirred for a further 3.5 hours. Further sodium cyanoborohydride (1.37 g) was then added and the mixture stirred for 18 hours. Yet more sodium cyanoborohydrida (1.37 g) was added and the mixture stirred for a further 3 hours. The mixture was then stripped and the residue treated with 10% w/v aqu/ NaHCO₃ and extracted with ether (3×150 ml). The combined extracts were washed with 10% w/v aqu. NaHCO₃ and with water (2×100 ml), dried over Na₂SO₄, stripped and dried under high vacuum to give the desired product (5.83 g).

(g) (E)-N-{1-Methyl-3-[3-(4-fluorophenoxy)phenyl]prop-2-enyl)acetohydroxamic acid The product from step (f) (5.83 g) and pyridine (3.71 g) were taken up in dichloromethane (75 ml), acetyl chloride (3.69 g) was added over 5 minutes, and the mixture then stirred for 2 hours. The mixture was then diluted with ether (150 ml), washed with 2 M aqu. HCl (3×100 ml). with satd. aqu. NaHCO₃ (2×200 ml) and with water (200 ml). dried over Na₂SO₄, and stripped to give the N,N-diacetyl derivative as a pale yellow oil. The latter was taken up in methanol (75 ml), anhy. potassium carbonate (5.91 g) was added, and the mixture stirred for ½ hour. The mixture was then filtered and the filtrate stripped to give a tan oil which was taken up in ether (200 ml), washed with water (150 ml), and extracted with 2 M aqu. NaOH (100 ml). The aqueous washings and extracts were combined and acidified with ether (3×100 ml), and the extracts washed with water (150 ml), dried over Na₂SO₄, and stripped to give a pale yellow oil. The latter crystallised on standing overnight at 0° C. in the presence of 40–60 pet.ether/ethyl acetate. The crystals were filtered off, washed with 40–60 pet.ether/ethyl acetate, recrystallised from ether/40–60 pet.ether and dried in air. Yield 3.30 g, mp 81°–83° C.

SYNTHETIC EXAMPLE 5

Preparation of N-{1,1-dimethyl-3-[3-(4-chlorophenoxy)phenyl]prop-2-enyl} acetohydroxamic acid (a) N-(1,1-Dimethylpropargyl)-0-benzoylacetohydroxamic acid 1.1-Dimethylpropargylamine (19 g, 10% water, Aldrich) was dissolved in benzene (100 ml) and dried over anhy. MgSO₄. Benzoyl peroxide (32.2 g, 25% water) was dissolved in methylene chloride (400 ml). dried over anhy. MgSO₄ and stripped. The benzene solution of the amine was then filtered on to the residual benzoyl peroxide and the mixture heated at 50° C. for 4 hours After cooling, 40–60 pet.ether (200 ml) was added, the mixture was filtered, and the filtrate stripped. The residue was taken up in 5% ether/40–60 pet.ether, refiltered, and the filtrate stripped to give the N-benzoylated derivative (17.0 g). The latter was dissolved in methylene chloride (100 ml) and pyridine (50 ml), acetyl chloride (10 ml), and DMAP (1 g) were added. The mixture was refluxed for 4 hours, then diluted with ether (200 ml), washed with 2 M aqu. HCl, with satd. aqu. NaHCO₃ and with water, dried over Na₂SO₄ and stripped. The residue was eluted through a silica gel column using 2% ether/methylene chloride and the eluate stripped and triturated with 40–60 pet.ether to give the desired product. Yield 8.0 g, mp 74°–75° C.

(b) N-(1,1-Dimethylallyl)-0-benzoylacetohydroxamic acid

N-(1,1-Dimethylpropargyl)-0-benzoylacetohydroxamic acid (5 g) was taken up in methanol, Lindlar catalyst (250 mg) was added, and the mixture stirred under hydrogen until uptake ceased (650 ml). The mixture was stripped to give the desired product.

(c) N-{1,1-Dimethyl-3-[3-(4-chlorophenoxy)phenyl]prop-2-enyl}acetohydroxamic acid A mixture of the product of step (a) (2.5 g), Pd(OAc)₂ (170mg), tri-o-tolylphosphine (0.45 g), triethylamine (10 ml). and 3-(4-chlorophenoxy)bromobenzene was heated for 19.5 hours at 140° C. After cooling, the mixture was washed with 2 M aqu. HCl (150 ml) and extracted with ether (200 ml). The extract was washed with satd. aqu. NaCl, dried over MgSO₄ and stripped. The residue was taken up in methanol (50 ml), anhy. potassium carbonate (1 g) was added, and the mixture stirred for ¼ hour. The mixture was then stripped, the residue partitioned between ether (150 ml) and water (150 ml), and the organic phase separated, washed with satd. aqu. NaCl, dried over MgSO₄ and stripped. The residue was eluted through a silica gel column using ether and the eluate stripped to give the desired product as a yellow oil (0.7 g).

PHARMACEUTICAL FORMULATION EXAMPLES

The following examples serve only to illustrate suitable formulations of the present invention and should in no way be construed as limitations thereof. The "active ingredient" in the formulations may be any compound or physiologically acceptable salt thereof in accordance with the invention.

Example A: Tablet

|  | Per tablet |
| --- | --- |
| Active Ingredient | 5.0 mg |
| Lactose | 82.0 mg |
| Starch | 10.0 mg |
| Povidone | 2.0 mg |
| Magnesium Stearate | 1.0 mg |

Mix together the active ingredient, lactose and starch. Granulate the powders using a solution of povidone in purified water. Dry the granules, add the magnesium stearate and compress to produce tablets (100 mg per tablet).

Example B: Ointment

| Active Ingredient | 1.0 g |
| --- | --- |
| White Soft Paraffin to | 100.0 g |

Disperse the active ingredient in a small volume of the vehicle. Gradually incorporate this into the bulk to produce a smooth, homogeneous product. Fill into collapsible metal tubes.

Example C: Cream for topical use

| Active Ingredient | 1.0 g |
| --- | --- |
| Polawax GP 200 | 20.0 g |
| Lanolin Anhydrous | 2.0 g |
| White Beeswax | 2.5 g |
| Methyl hydroxybenzoate | 0.1 g |
| Distilled Water to | 100.0 g |

Heat the Polawax, beeswax and lanolin together at 60° C. Add a solution of methyl hydroxybenzoate. Homogenise using high speed stirring. Allow the temperature to fall to 50° C. Add and disperse the active ingredient. Allow to cool with slow speed stirring.

Example D: Lotion for topical use

| Active Ingredient | 1.0 g |
| --- | --- |
| Sorbitan Monolaurate | 0.6 g |
| Polysorbate 20 | 0.6 g |
| Cetostearyl Alcohol | 1.2 g |
| Glycerin | 6.0 g |
| Methyl Hydroxybenzoate | 0.2 g |
| Purified Water B.P. to | 100.00 ml |

The methyl hydroxybenzoate and glycerin were dissolved in 70 ml of the water at 75° C. The sorbitan monolaurate, Polysorbate 20 and catostearyl alcohol were melted together at 75° C. and added to the aqueous solution. The resulting emulsion was homogenised, allowed to cool with continuous stirring and the active ingredient added as a suspension in the remaining water. The whole was stirred until homogeneous.

Example E: Eye drops

| Active Ingredient | 0.5 g |
| --- | --- |
| Methyl Hydroxybenzoate | 0.01 g |
| Propyl Hydroxybenzoate | 0.04 g |
| Purified Water B.P. to | 100.00 ml |

The methyl and propyl hydroxybenzoates were dissolved in 70 ml of purified water at 75° C. and the resulting solution allowed to cool. The active ingredient was then added and the solution made up to 100 ml with purified water. The solution was sterilised by filtration through a membrane filter of 0.22 μm pore size and packed aseptically into suitable sterile containers.

Example F: Injectable solution

| Active Ingredient | 10.0 mg |
| --- | --- |
| Water for Injections B.P. to | 1.0 ml |

The active ingredient was dissolved in half of the Water for Injections and then made up to volume and sterilised by filtration. The resulting solution was distributed into ampoules under aseptic conditions.

Pulmonary formulations

In Examples G and H below, the "active ingredient" may be any compound of formula (I) or a physiologically acceptable salt thereof, for example, the compounds of Synthetic Examples 1 to 3.

Example G: Powder capsules for inhalation

| Active Ingredient (0.5–7.0 μm powder) | 4 mg |
| --- | --- |
| Lactose (30–90 μm powder) | 46.0 mg |

The powders were mixed until homogeneous and filled into suitably sized hard gelatin capsules (50 mg per capsule).

Example H: Inhalation aerosol

| Active Ingredient (0.5–7.0 μm powder) | 200 mg |
| --- | --- |
| Sorbitan Trioleate | 100 mg |
| Saccharin Sodium (0.5–7.0 μm powder) | 5 mg |
| Methanol | 2 mg |
| Trichlorofluoromethane | 4.2 g |
| Dichlorodifluoromethane to | 10.0 ml |

The sorbitan trioleate and menthol were dissolved in the trichlorofluoromethane. The saccharin sodium and active ingredient were dispersed in the mixture which was then transferred to a suitable aerosol canister and the dichlorofluoromethane injected through the valve system. This composition provides 2 mg of active ingredient in each 100 μl dose.

Biological Examples

The following data are provided with a view to indicating the improved effectiveness of the compounds of the present invention over those of the prior art, in particular the analogous compound (E)-N-[3-(3-phenoxyphenyl) prop-2-enyl]acetohydroxamic acid of the earlier European application wherein the methylene carbon adjacent the nitrogen is unsubstituted.

In the following, section A demonstrates the uptake of compounds according to the present invention and their duration times in the plasma. Section B demonstrates the effectiveness of the compounds of the invention in inhibiting the stimulated synthesis of LTB$_4$ ex vivo and section C indicates their in vitro activity as inhibitors of 5-LO and CO (N B. LTB$_4$ (leucotriene B$_4$) and TXB$_2$ (thromboxane B$_2$) are products derived from 5-lipoxygenase and cyclo-oxygenase respectively).

A. Maximum plasma concentration obtained after administration to rabbits of 10 mg/kg PO and time for plasma concentration to fall to 50% of maximum value obtained after administration (E)-N-[1-Methyl-3-(3-phenoxyphenyl)prop-2-enyl-]acetohydroxamic acid 0.46 μg/ml (10.7 h)

(E)-N-{Methyl-2-[3-(4-methylphenoxy)phenyl]prop-2-enyl}acetohydroxamic acid 0.07 μg/ml (4.3 h)

(E)-N-{1-Methyl-3-[3-(4-t-butylphenoxy)phenyl]prop-2-enyl}acetohydroxamic acid 0.16 μg.ml (>24 h)

(E)-N-{1-Methyl-3-[3-(4-chlorophenoxy)phenyl]prop-2-enyl}acetohydroxamic acid 0.93 μg/ml (>24 h)

(E)-N-{1-Methyl-3-[3-(4-bromophenoxy)phenyl]prop-2-enyl}acetohydroxamic acid 0.71 μg/ml (>24 h)

(E)-N-{1-Methyl-3-[3-(3-trifluoromethyl)phenyl]prop-2-enyl}acetohydroxamic acid 0.84 μg/ml (>24 h)

(E)-N-{1-Methyl-3-[3-(3,5-dichlorophenoxy)phenyl]-prop-2-enyl}acetohydroxamic acid 1.90 μg/ml (>24 h)

(E)-N-{1-Methyl-3-[3-(4-fluorophenoxy)phenyl]prop-2-enyl}acetohydroxamic acid 1.07 μg/ml (11.3 h)

B. Time for stimulated LTB$_4$ synthesis ex vivo to return to 50% of original value after administration to rabbits of 10 mg/kg PO (E)-N-[1-Methyl-3-(3-phenoxyphenyl)prop-2-enyl-]acetohydroxamic acid 22.6 h (E)-N-{1-Methyl-3-[3-(4-methylphenoxy)phenyl]prop-2-enyl}acetohydroxamic acid <50%

(E)-N-{1-Methyl-3-[3-(4-t-butylphenoxy)phenyl]prop-2-enyl}acetohydroxamic acid 2.4 h (E)-N-{1-Methyl-3-[3-(4-chlorophenoxy)phenyl]prop-2-enyl}acetohydroxamic acid >24 h (E)-N-{1-Methyl-3-[3-(4-bromophenoxy)phenyl]prop-2-enyl}acetohydroxamic acid >24 h (E)-N-{1-Methyl-3-[3-(3-trifluoromethylphenoxy)-phenyl]prop-2-enyl}acetohydroxamic acid >24 h (E)-N-{1-Methyl-3-[3-(3,5-dichlorophenoxy)phenyl]-prop-2-enyl}acetohydroxamic acid >24 h (E)-N-{1-Methyl-3-[3-(4-fluorophenoxy)phenyl]prop-2-enyl}acetohydroxamic acid 24.0 h (E)-N-{1-Methyl-3-[3-(2,4-difluorophenoxy)phenyl]-prop-2-enyl}acetohydroxamic acid 20.7 h C. In vitro inhibition of 5-lipoxygenase (5-LO) and cyclo-oxygenase (CO)

Blood from normal aspirin-free volunteers was centrifuged to separate leukocytes from red cells and platelets. The leukocytes were homogenised and 5 μM arachidonic acid added, followed by incubation at 37° C. for 5 minutes. The reaction was stopped by boiling and radioimmunoassays conducted for LTB$_4$ and TXB$_2$. Results were calculated as IC$_{50}$ (μM) activity against each enzyme.

(E)-N-[1-Methyl-3-(3-phenoxyphenyl)prop-2-enyl-]acetohydroxamic acid

| 5-LO activity (μM) | 0.08 |
|---|---|
| CO activity (μM) | 1.00 |

(E)-N-{1-Methyl-3-[3-(4-fluorophenoxy)phenyl]prop-2-enyl}acetohydroxamic acid:

| 5-LO activity (μM) | 0.20 |
|---|---|
| CO activity (μM) | — |

(E)-N-{1-Methyl-3-[3-(4-t-butylphenoxy)phenyl]prop-2-enyl}acetohydroxamic acid:

| 5-LO activity (μM) | 0.50 |
|---|---|
| CO activity (μM) | — |

(E)-N-{1-Methyl-3-[3-(4-chlorophenoxy)phenyl]prop-2-enyl}acetohydroxamic acid:

| 5-LO activity (μM) | 0.08 |
|---|---|
| CO activity (μM) | >1.00 |

(E)-N-{1Methyl-3-[3-(4-bromophenoxy)phenyl]prop-2-enyl}acetohydroxamic acid:

| 5-LO activity (μM) | 0.01 |
|---|---|
| CO activity (μM) | 0.18 |

(E)-N-{1-methyl-3-[3-(3-trifluoromethyl)phenyl]prop-2-enyl}acetohydroxamic acid:

| 5-LO activity (μM) | 0.11 |
|---|---|
| CO activity (μM) | >1.00 |

(E)-N-{1-Methyl-3-[3-(3,5-dichlorophenoxy)phenyl]-prop-3-enyl}acetohydroxamic acid:

| 5-LO activity (μM) | 0.40 |
|---|---|
| CO activity (μM) | — |

(E)-N-{1-Methyl-3-[3-(4-fluorophenoxy)phenyl]prop-2-enyl}acetohydroxamic acid:

| 5-LO activity (μM) | 0.30 |
|---|---|
| CO activity (μM) | — |

These figures for 5-LO and CO inhibition compare favourably with those of (E)-N-[3-(3-phenoxyphenyl)-prop-2-enyl]acetohydroxamic acid, the analogous compound of the earlier European application wherein the methylene carbon adjacent the nitrogen is unsubstituted, which compound represents the closest known prior art to the compounds of the present invention. The unsubstituted compound of the earlier application has a 5-LO activity of 0.06 μM and a CO activity of 1.0 μM when tested against the assay described in section C.

We claim:

1. A compound of formula (II)

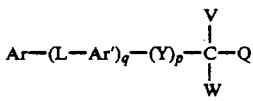 (II)

wherein q is 1 and p is 1;

Ar is phenyl optionally substituted by one or more substituents independently selected from $C_{1-4}$ alkyl (which may be substituted by one or more halogen atoms) and halogen;

L is —O—;

Ar' is 1,3- or 1,4-phenylene;

Y is (E)—CH=CH—;

V is hydrogen or $C_{1-4}$ alkyl;

W is $C_{1-4}$ alkyl; and

Q is a moiety of formula

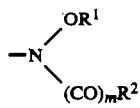

wherein m is 1, $R^1$ is hydrogen, and $R^2$ is hydrogen or $C_{1-4}$ alkyl;

and salts thereof.

2. A compound of formula (II) as shown in claim 1, wherein q is 1 and p is 1;

Ar is phenyl optionally substituted by one or more substituents independently selected from methyl, trifluoromethyl, bromo, chloro, and fluoro;

L is —O—;

Ar' is 1,3-phenylene;

Y is (E)—CH=CH—;

V is hydrogen;

W is methyl; and

Q is a moiety of the formula shown in claim 1 wherein m is 1, $R^1$ is hydrogen, and $R^2$ is methyl;

and salts thereof.

3. A compound of formula (II) which is selected from the following:

(E)-N-[1-Methyl-3-(3-phenoxyphenyl)prop-2-enyl]acetohydroxamic acid;

(E)-N-{1-Methyl-3-[3-(4-methylphenoxy)phenyl]prop-2-enyl}acetohydroxamic acid;

(E)-N-{1-Methyl-3-[3-(4-t-butylphenoxy)phenyl]prop-2-enyl}acetohydroxamic acid;

(E)-N-{1-Methyl-3-[3-(4-chlorophenoxy)phenyl]prop-2-enyl}acetohydroxamic acid;

(E)-N-{1-Methyl-3-[3-(4-bromophenoxy)phenyl]prop-2-enyl}acetohydroxamic acid;

(E)-N-{1-Methyl-3-[3-(3-trifluoromethylphenoxy)phenyl]prop-2-enyl}acetohydroxamatic acid;

(E)-N-{1-Methyl-3-[3-(3,5-dichlorophenoxy)phenyl]prop-2-enyl}acetohydroxamic acid;

(E)-N-{1-Methyl-3-[3-(4-fluorophenoxy)phenyl]prop-2-enyl}acetohydroxamic acid; and (E)-N-{1-Methyl-3-[3-(2,4-difluorophenoxy)phenyl]prop-2-enyl}acetohydroxamic acid;

in either its (+) or (−) enantiomeric form or as a mixture thereof in any proportions, and salts thereof.

4. A pharmaceutical formulation comprising a compound of formula (II) as claimed in claim 1 or a pharmaceutically acceptable salt thereof, a pharmaceutically acceptable carrier thereof, and, optionally, one or more other pharmacologically active agents.

5. A formulation according to claim 4, wherein the compound of formula (II) is as claimed in claim 2 or is a pharmaceutically acceptable salt thereof.

6. A formulation according to claim 4, wherein the compound of formula (II) is selected from the compounds named in claim 3 or is a pharmaceutically acceptable salt thereof.

7. A formulation according to claim 4, wherein the formulation is adapted for pulmonary administration and the compound of formula (II) is (E)-N-{1-Methyl-3-[3-(4-chlorophenoxy)phenyl]prop-3-enyl}acetohydroxamic acid; or (E)-N-{1-Methyl-3-[3-(4-fluorophenoxy)phenyl]prop-3-enyl}acetohydroxamic acid;

in either its (+) or (−) enantiomeric form or as a mixture thereof in any proportions, or a pharmaceutically acceptable salt thereof.

8. A method of therapeutically or prophylactically treating an inflammitory condition in a mammal, which comprises administering to said mammal an effective therapeutic or prophylactic amount of the compound or a pharmaceutically acceptable salt of claim 1, 2 or 3.

9. The compound N-[1-(3-phenoxyphenyl)ethyl]acetohydroxamic acid.

10. A pharmaceutically acceptable salt of N-[1-(3-phenoxyphenyl)ethyl]acetohydroxamic acid.

11. A method as claimed in claim 8, wherein said mammal is human.

* * * * *